(12) United States Patent
Liu

(10) Patent No.: US 7,377,168 B2
(45) Date of Patent: May 27, 2008

(54) WIRELESS SENSOR ANTENNA CONFIGURATION

(75) Inventor: James Zt Liu, Hudson, NH (US)

(73) Assignee: Honeywell International Inc., Morristown, NJ (US)

( * ) Notice: Subject to any disclaimer, the term of this patent is extended or adjusted under 35 U.S.C. 154(b) by 176 days.

(21) Appl. No.: 11/300,090

(22) Filed: Dec. 13, 2005

(65) Prior Publication Data

US 2007/0131032 A1   Jun. 14, 2007

(51) Int. Cl.
H03H 9/25 (2006.01)
G01L 11/04 (2006.01)
(52) U.S. Cl. .......................................... 73/579; 73/703
(58) Field of Classification Search .............. 73/579, 73/703, 724; 331/65; 310/313 R, 313 B; 33/65
See application file for complete search history.

(56) References Cited

U.S. PATENT DOCUMENTS

| | | | |
|---|---|---|---|
| 3,092,806 A | 6/1963 | Field | 340/58 |
| 3,906,340 A | 9/1975 | Wingfield et al. | 324/57 Q |
| 4,186,749 A * | 2/1980 | Fryer | 600/561 |
| 4,409,586 A | 10/1983 | Hochstein | |
| 5,663,504 A | 9/1997 | Kluft | |
| 6,278,379 B1 * | 8/2001 | Allen et al. | 340/870.16 |
| 6,662,642 B2 * | 12/2003 | Breed et al. | 73/146 |
| 7,165,455 B2 * | 1/2007 | Magee et al. | 73/650 |
| 2005/0046558 A1 | 3/2005 | Buenz et al. | |
| 2007/0074579 A1 * | 4/2007 | Cook et al. | 73/718 |
| 2007/0107522 A1 * | 5/2007 | Oikawa et al. | 73/754 |

FOREIGN PATENT DOCUMENTS

| | | |
|---|---|---|
| DE | 19602048 A1 | 7/1997 |
| WO | WO 00/50849 A1 | 8/2000 |

OTHER PUBLICATIONS

Kyu-Ho Shin et al., Implantable Flexible Wireless Pressure Sensor Module, Sensors, 2004, Piscataway, NJ, USA, IEEE, Oct. 2004, pp. 844-847, XP010793537.

* cited by examiner

Primary Examiner—John E Chapman
(74) Attorney, Agent, or Firm—Richard H. Krukar; Luis M. Ortiz; Kermit D. Lopez

(57) ABSTRACT

Many sensors could be used in a passive wireless mode. These include RLC, acoustic wave and magneto-elastic sensors. These types of sensors are designed to exhibit a change in fundamental frequency when exposed to environmental factors such as temperature, pressure, or chemicals. An interrogation circuit can inductively couple to the sensor and measure the change in fundamental frequency. The change can be used to measure the environmental factor. Sensor sensitivity and inductive coupling efficiency can be competing design constraints. A driver, electrically connected to the sensor and inductively coupled to the interrogation circuit, can relax the constraints. The driver, however, can introduce noise into the sensor. The sensor can be shielded using physical and geometric techniques to reduce the noise.

16 Claims, 5 Drawing Sheets

WIRELESS SENSOR ANTENNA CONFIGURATION

TECHNICAL FIELD

Embodiments relate to sensors, sensor systems, and wireless interrogation. Embodiments also relate to passive wireless sensors and acoustic wave sensors.

BACKGROUND OF THE INVENTION

A variety of sensors are utilized to detect conditions, such as pressure and temperature. The ability to detect pressure and/or temperature is an advantage to any device exposed to variable pressure conditions, which can be severely affected by these conditions. An example of such a device is a catheter, which of course, can experience variations in both temperature and pressure. Many different techniques have been proposed for sensing the pressure and/or temperature passively and wirelessly. These technologies include LC tank, RC or RLC oscillator type, acoustic wave sensor, and magneto-elastic sensor.

Acoustic wave devices often have one or two transducers arranged on a piezoelectric substrate. A transducer can convert an electrical input signal into an acoustic signal. The acoustic wave device can then alter the acoustic signal as it propagates through, or along, the substrate. A transducer can also convert the acoustic signal into an electrical signal. One common use of acoustic wave devices is conditioning or filtering signals, such as filtering the electrical signal received by a cellular telephone, because acoustic wave devices can be extremely good and inexpensive signal filters.

Acoustic wave devices are also used as sensors. The piezoelectric substrate is sensitive to environmental conditions. It can expand or contract with the temperature. Pressure can cause it to flex. Some chemical sensors are based on acoustic wave devices such that exposure to a chemical, such as water or alcohol, can introduce mass-loading effect. Mass-loading to the substrate of an acoustic wave device can change its acoustic properties. The changing acoustic properties can affect the acoustic signals which become electrical signals at the transducers. As such, acoustic wave devices have been used to measure temperature, pressure, chemical densities, and other environmental properties.

FIG. 4, labeled as "prior art", illustrates one type of acoustic wave device known as a surface acoustic wave device (SAW). In a SAW the acoustic waves propagate along the surface of the substrate 401. The illustrated SAW has an input transducer 402, an output transducer 403, and a substrate 401. An input electrical signal enters the input transducer 402, becomes an acoustic signal, and travels over the substrate surface to the output transducer 403. The acoustic signal can be transformed by the substrate 401 as it travels over the substrate surface. The output transducer 403 then converts the acoustic signal into an output electrical signal. Essentially, the SAW transforms the input electrical signal into the output electrical signal.

FIG. 5, labeled as "prior art", illustrates another type of acoustic wave device called a bulk acoustic wave device (BAW). In a BAW the acoustic signal travels through the substrate 501. A signal between the first lead 503 and the second lead 505 appears as a voltage difference between the first electrode 502 and second electrode 504. The voltage difference causes the substrate 501 to expand or contract. Similarly, expansions and contractions of the substrate 501, as can be caused by pressure, cause a voltage difference between the first electrode 502 and second electrode 504. The voltage difference then can then pass away from the BAW along the first lead 503 and the second lead 505.

Yet another type of sensor is the RLC sensor. RLC is shorthand for "resistor, inductor, and capacitor". An RLC sensor is a sensor that, as with the acoustic wave devices discussed above, changes its fundamental frequency based on environmental conditions such as pressure or temperature. In some sensors, the resistive element changes with environmental conditions. In a resistive pressure sensor environmental pressure changes the resistance of at least one of the resistors. The changed resistance results in a changed fundamental frequency. Temperature can also cause resistance changes. A positive temperature coefficient (PTC) resistor increases resistance as the temperature increases. A negative temperature coefficient (NTC) resistor decreases resistance as the temperature increases.

Another use of PTC and NTC resistors is temperature compensation. For example, an RLC pressure sensor can have a capacitor that changes capacitance when pressure changes and when temperature changes. As such, the pressure sensor gives poor results is the temperature isn't constant and ideal. A temperature sensitive resistor can be used to compensate for the capacitor's temperature sensitivity. An RLC sensor that uses a pressure sensitive capacitor to sense pressure is a capacitive pressure sensor. An RLC sensor that uses a pressure sensitive inductor to sense pressure is an inductive pressure sensor.

An RLC sensor has no electrical components other than resistors, capacitors, and inductors. An LC sensor is a type of RLC sensor without resistors. An RC sensor is a type of RLC sensor without inductors. The term "LC tank" is synonymous with "LC" while the term "tank" can refer to either RLC or LC. Those skilled in the arts of analog electronics or analog sensors are familiar with using RLC, LC, RC, LC tank, and tank circuits as sensors and as passive sensors. They are also familiar with NTC and PTC resistors, the use of those resistors as sensing elements, and the use of those resistors as compensation elements.

Another sensor element is the magnetoelastic or magnetostrictive transducer. In a magnetoelastic or magnetostrictive transducer, the change in the position of a sensing shaft creates stress in the stress-sensitive core. The permeability of the core material alters with stress, effecting the inductance of the winding wound around the core. The inductance is a function of the shaft's position. The sensors fundamental frequency changes when the inductance changes. Those skilled in the art of sensors are familiar with the magnetoelastic or magnetostrictive transducer.

Many sensors can not be advantageously employed unless an interrogation circuit is also employed. These technologies include LC tank, RC or RLC oscillator type, acoustic wave sensor, and magneto-elastic sensor. An interrogation circuit is a circuit that creates an interrogation signal that is passed to the sensor. The sensor then returns a response signal or affects the interrogation signal in some way. For example, an electronic thermometer can accept an interrogation signal comprising power and ground while returning a voltage proportional to the temperature as a response signal. Alternatively, a material that changes its electrical resistance can be used as a temperature sensor. The interrogation signal can be power and ground voltages while the current passing through the circuit is the response signal.

FIG. 6, labeled as prior art, illustrates an inductively coupled interrogation circuit 601. A function generator 603 can produce a signal. One such signal is a repeating voltage ramp. Those skilled in the arts of electronics or signaling often call this a saw tooth signal. The saw tooth signal can be passed to a voltage controlled oscillator (VCO) 604. A VCO 604 produces a signal with a frequency dependent on an input voltage. Passing a saw tooth signal to the VCO 604 causes the VCO 604 to produce an interrogation signal that repeatedly sweeps through a range of frequencies. The interrogation signal is passed to an inductor 602, a grid dip oscillator (GDO) 108, and a phase locked loop (PLL) 605. The inductor 602 can inductively couple the interrogation signal into an inductive load (not shown).

The efficiency with which the interrogation signal is coupled into an inductive load depends on the inductive load and the interrogation signal frequency. Many circuits, including inductive loads, have a fundamental frequency. When the interrogation signal frequency matches the fundamental frequency, the coupling is maximized. As the interrogation signal sweeps through a frequency range, the fundamental frequency can be detected by the GDO 108 because the voltage across the inductor 602 drops to a minimum value at the inductive load's fundamental frequency. The GDO 108 signals the PLL 605 at the fundamental frequency. A PLL 605 is an oscillator that can lock onto and follow a source signal. As such, the PLL 605 locks onto and follows the interrogation signal. When signaled by the GDO 108, however, the PLL 605 can stop following the interrogation signal and remain producing a locked signal at the inductive load's fundamental frequency. The locked signal is passed to a frequency counter 606.

The system of FIG. 6 illustrates an interrogation circuit that can measure the fundamental frequency of an inductive load. Similar interrogation circuits are disclosed in U.S. Pat. Nos. 3,092,806 and 3,906,340. U.S. Pat. Nos. 3,092,806 and 3,906,340 are incorporated by reference into this document.

Some acoustic wave devices can inductively couple with an interrogation circuit. However, high inductive coupling efficiency and high sensor sensitivity can be competing design goals. Devices designed for coupling efficiency can lack sensitivity. Sensitive devices can couple poorly. A driving element, or driver, can improve the sensor. The driver is electrically connected to the acoustic wave device and inductively coupled to interrogation circuit. The problem, however, is that the acoustic wave device and the driver can both inductively couple with the interrogation circuit. This can lead to a noisy sensor reading. Another concern is that the driver and the acoustic wave device can inductively couple with one another, creating another source of noise in the sensor readings.

Spiral inductors are inductors that are formed on a planar substrate. They have been formed and used on single layer circuit boards and, in some specialized circumstances, in integrated circuits. Those skilled in the arts of radio frequency circuits, circuit layout, or inductors are aware of the design and use of spiral inductors.

Aspects of the embodiments directly address the shortcoming of current technology by using spiral inductors as drivers and using physical and geometric mechanisms to shield the acoustic wave device from various sources of inductive coupling.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

It is therefore an aspect of the embodiments to provide a sensor that contains and acoustic wave device electrically connected to a spiral inductor and to use an interrogation circuit to interrogate the sensor. The interrogation circuit, containing a grid dip oscillator (GDO), inductively couples with the spiral inductor and measures the fundamental frequency. Surface acoustic wave (SAW) devices and bulk acoustic wave (BAW) devices are examples of acoustic wave devices. Shielding techniques are used to inhibit the acoustic wave device from becoming inductively coupled with other elements such as the spiral inductor or the interrogation circuit.

It is an aspect of certain embodiments to use a shielding technique wherein a guard ring can be placed around either the acoustic wave device or the spiral inductor. A guard ring is a conductive trace surrounding, or nearly surrounding, a circuit element. The guard ring is usually connected to circuit ground and thereby helps prevent noise from reaching the enclosed circuit element or from escaping from the enclosed circuit element. Guard rings are most effective in protecting coplanar elements, meaning they geometrically lie substantially on the same plane, from one another. In many cases, circuit elements are exposed to noise sources that are not coplanar, in which case a shield of conductive material is used. The shield substantially encloses the circuit elements. A guard ring can be thought of as a two dimensional shield that works in special circumstances.

It is an aspect of some embodiments to use geometric shielding. Historically, the simplest type of shielding, called "one over r squared shielding" is to place a sensitive component far from noise sources. Distance, however, is rarely available in a compact system and rarely appropriate for real world situations. A small amount of distance can have a large effect in some circumstances. As dictated by the laws of physics, the fundamental frequency, discussed above, is inversely related to a fundamental wavelength. Separating the acoustic wave device and the spiral inductor by a few fundamental wavelengths can have a large effect on inductive coupling.

Inductive coupling occurs most efficiently when the electromagnetic fields of two or more inductive circuit elements line up. Misaligning the fields can significantly reduce inductive coupling. Rotation and lateral shifts can cause significant misalignment and thereby reduce the inductive coupling.

BRIEF DESCRIPTION OF THE DRAWINGS

The accompanying figures, in which like reference numerals refer to identical or functionally similar elements throughout the separate views and which are incorporated in and form a part of the specification, further illustrate the present invention and, together with the background of the invention, brief summary of the invention, and detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof. In general, the figures are not to scale.

Figure 1:
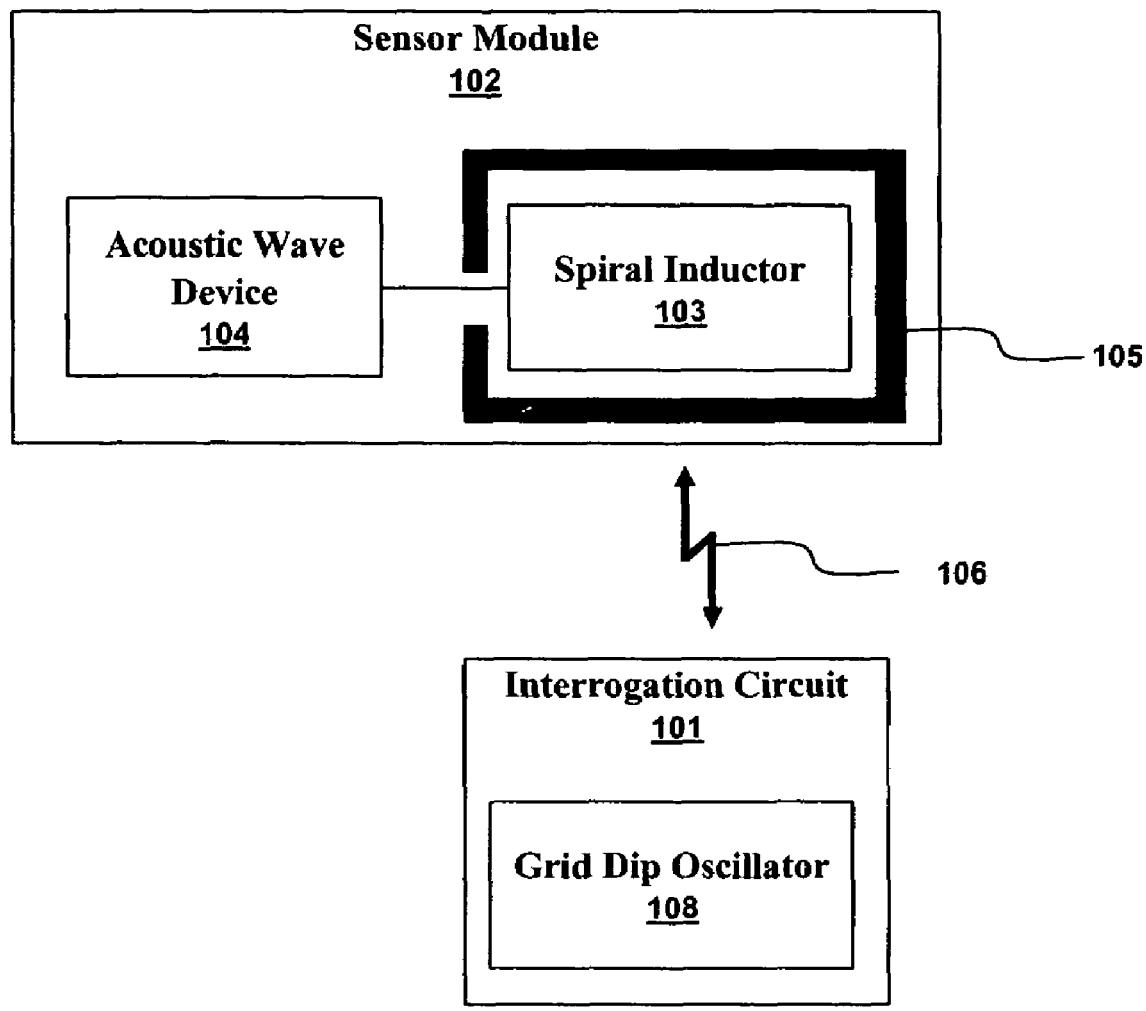
FIG. 1 illustrates a sensor module inductively coupled to an interrogation circuit in accordance with an embodiment.

FIG. 1 illustrates a sensor module 102 inductively coupled to an interrogation circuit 101 in accordance with an embodiment. As discussed above, the interrogation circuit 101 can contain a grid dip oscillator (GDO) 108. The interrogation circuit 101 is inductively coupled to a spiral inductor 103 with the inductive coupling indicated by a two headed arrow 106. The spiral inductor 103 is surrounded by a guard ring 105 to minimize the coupling between the spiral inductor 103 and an acoustic wave device 105 to which it is electrically connected. In the system of FIG. 1, the acoustic wave device is open to noise sources other than the spiral inductor 103. Furthermore, the interrogation circuit 101 must be physically arranged to defeat the shielding properties of the guard ring 105 such as placing them on different planes and ensuring that the fields otherwise align.

Figure 2:
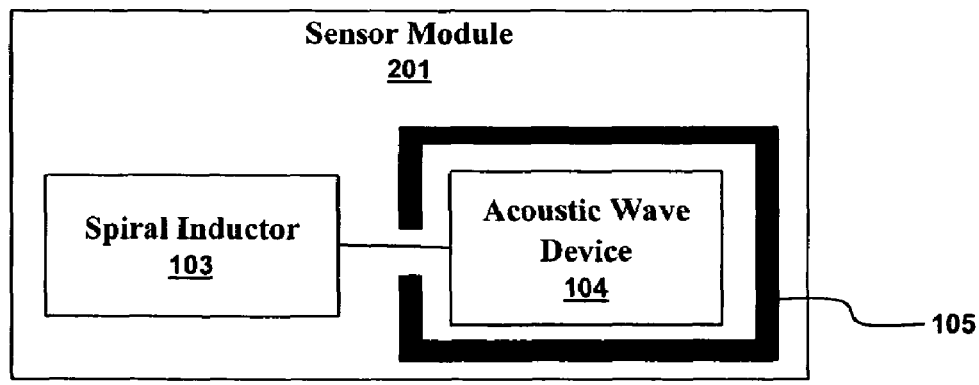
FIG. 2 illustrates a sensor module with a guard ring around an acoustic wave device in accordance with an embodiment.

FIG. 2 illustrates a sensor module 201 with a guard ring 105 around an acoustic wave device 104 in accordance with an embodiment. In the system of FIG. 2, the acoustic wave device 104 is shielded from many sources of inductive coupling.

Figure 3:
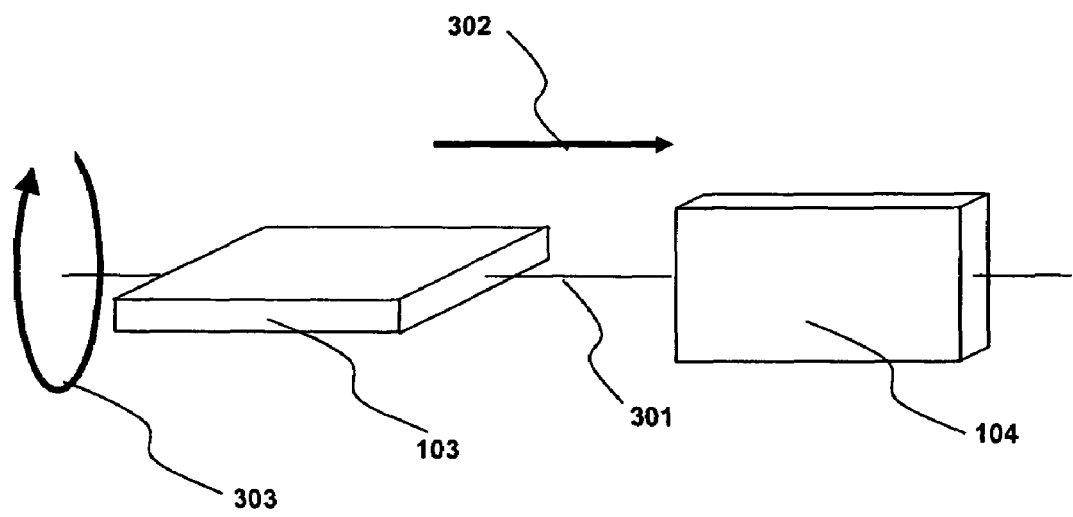
FIG. 3 illustrates an acoustic wave device laterally displaced and rotated in relation to a spiral inductor in accordance with an embodiment.
Figure 4:
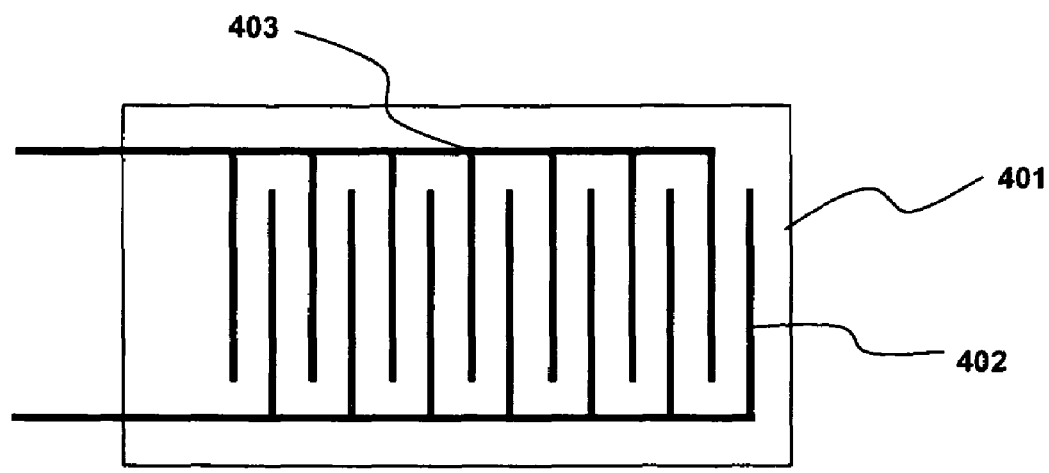
FIG. 4, labeled as "prior art", illustrates one type of acoustic wave device known as a surface acoustic wave device (SAW)
Figure 5:
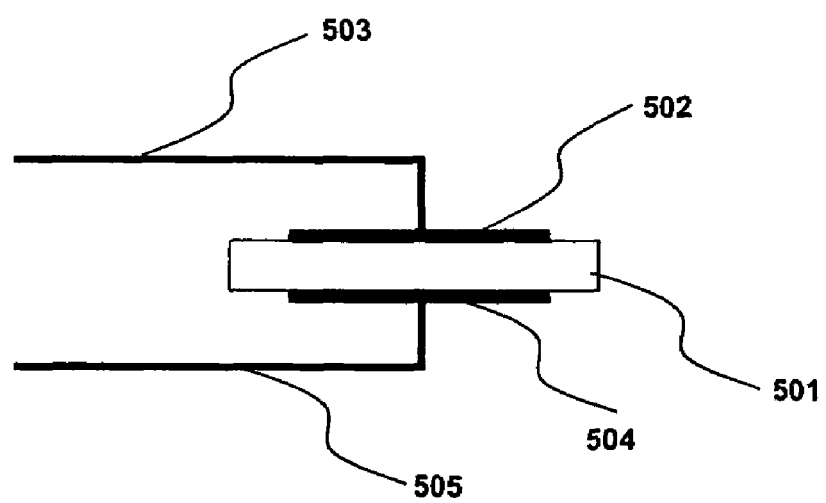
FIG. 5, labeled as "prior art", illustrates another type of acoustic wave device called a bulk acoustic wave device (BAW)
Figure 6:
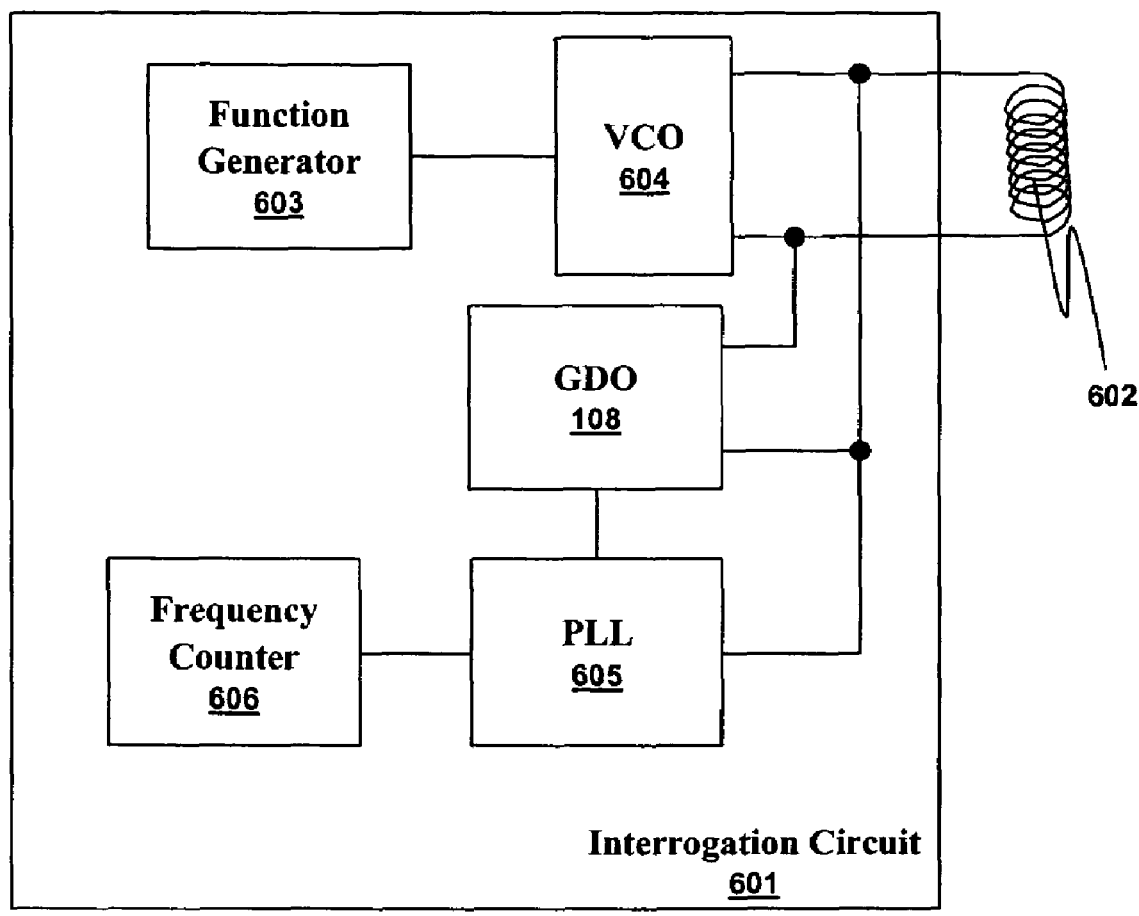
FIG. 6, labeled as prior art, illustrates an inductively coupled interrogation circuit 601.

FIG. 3 illustrates an acoustic wave device 104 laterally displaced and rotated in relation to a spiral inductor 103 in accordance with an embodiment. The plane of the acoustic wave device 104 is rotated approximately 90 degrees from that of the spiral inductor 103. The circling arrow 303 indicates that the planes are rotated in relation to one another. The straight arrow 302 indicates lateral displacement. The spiral inductor 103 and the acoustic wave device 104 are shown sharing a central axis 301. More generally, the devices do not need to share a central axis 301. Lateral displacement means "moved" but does not mean "moved along an axis". Furthermore, the illustration shows 90 degrees of rotation, which is optimal. In practice, angles between 85 and 95 degrees will work well while angles between 60 and 120 degrees can provide acceptable results.

Figure 7:
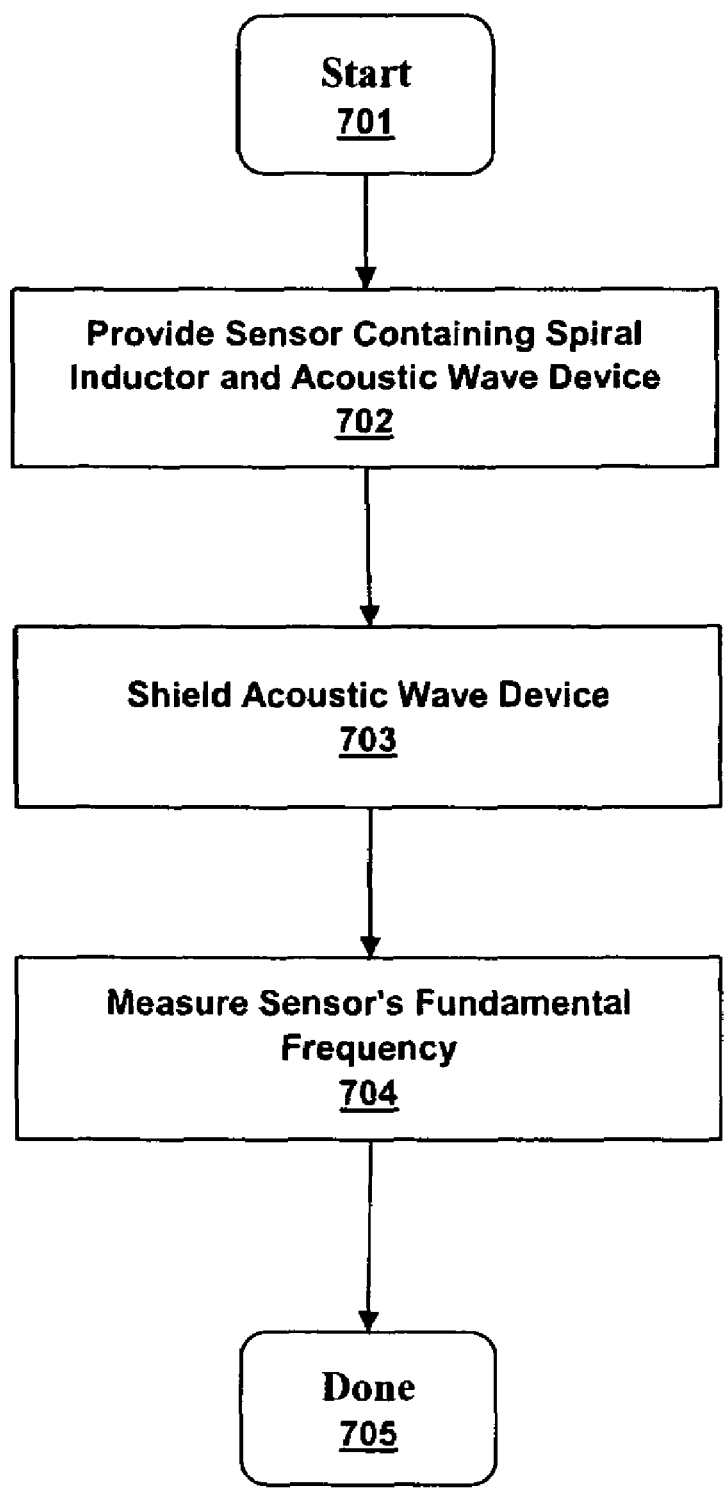
FIG. 7 illustrates a high level flow diagram of using a shielded sensor.

FIG. 7 illustrates a high level flow diagram of using a shielded sensor. After the start 701 a sensor containing a spiral inductor and an acoustic wave device is provided 702. The acoustic wave device is then shielded 703. For example, the acoustic wave device can be rotated and displaced laterally with respect to the spiral inductor. The sensor's fundamental frequency is then measured 704. An interrogation circuit containing a GDO can be used for the fundamental frequency measurement. Finally, the process is done 705.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A system comprising:
    a sensor comprising an acoustic wave device electrically connected to a spiral inductor wherein the sensor has a fundamental frequency that changes in response to environmental factors;
    an interrogation circuit that measures the fundamental frequency wherein the interrogation circuit is inductively coupled to the spiral inductor, and wherein the interrogation circuit comprises a grid dip oscillator; and
    a shield inhibiting inductive coupling to the acoustic wave device.

2. The system of claim 1 wherein the spiral inductor and the acoustic wave device are coplanar and wherein the shield is a guard ring surrounding the spiral inductor.

3. The system of claim 2 wherein the acoustic wave device is a surface acoustic wave device.

4. The system of claim 2 wherein the acoustic wave device is a bulk acoustic wave device.

5. The system of claim 1 wherein the spiral inductor and the acoustic wave device are coplanar and wherein the shield is a guard ring surrounding the acoustic wave device.

6. The system of claim 5 wherein the acoustic wave device is a surface acoustic wave device.

7. The system of claim 5 wherein the acoustic wave device is a bulk acoustic wave device.

8. The system of claim 1 wherein the shield comprises a conductive material enclosing the acoustic wave device.

9. A method comprising:
    providing a sensor comprising a passive sensor electrically connected to a spiral inductor wherein the sensor has a fundamental frequency that changes in response to environmental factors and wherein the passive sensor comprises a surface acoustic wave device;
    shielding the passive sensor from inductive coupling; and
    measuring the fundamental frequency with an interrogation circuit inductively coupled to the spiral inductor wherein the interrogation circuit comprises a grid dip oscillator.

10. The method of claim 9 wherein shielding comprises:
    rotating the passive sensor in relation to the spiral inductor and the interrogation circuit; and
    laterally displacing the passive sensor from the spiral inductor and the interrogation circuit.

11. The method of claim 9 wherein shielding comprises surrounding the spiral inductor with a guard ring wherein the spiral inductor and the acoustic wave device are coplanar.

12. The method of claim 9 wherein shielding comprises surrounding the passive sensor with a guard ring wherein the spiral inductor and the acoustic wave device are coplanar.

13. The method of claim 9 wherein shielding comprises enclosing the passive sensor in a shield comprising conductive material.

14. The method of claim 10 wherein shielding comprises surrounding the spiral inductor with a guard ring wherein the spiral inductor and the acoustic wave device are coplanar.

15. The method of claim 10 wherein shielding comprises surrounding the passive sensor with a guard ring wherein the spiral inductor and the acoustic wave device are coplanar.

16. The method of claim 10 wherein shielding comprises enclosing the passive sensor in a shield comprising conductive material.

* * * * *